(12) United States Patent
Aldenkortt

(10) Patent No.: US 7,319,164 B2
(45) Date of Patent: Jan. 15, 2008

(54) 5-AZIDO-LAEVULINIC ACID, METHOD FOR THE PRODUCTION THEREOF AND ITS USE

(76) Inventor: Sven Aldenkortt, Pilziggrundstrasse 54, D-97076, Würzburg (DE)

( * ) Notice: Subject to any disclaimer, the term of this patent is extended or adjusted under 35 U.S.C. 154(b) by 451 days.

(21) Appl. No.: 10/250,708

(22) PCT Filed: Jan. 8, 2002

(86) PCT No.: PCT/DE02/00074

§ 371 (c)(1),
(2), (4) Date: Jan. 22, 2004

(87) PCT Pub. No.: WO02/053532

PCT Pub. Date: Jul. 11, 2002

(65) Prior Publication Data

US 2006/0086443 A1    Apr. 27, 2006

(30) Foreign Application Priority Data

Jan. 8, 2001    (DE) ................. 101 01 317

(51) Int. Cl.
C07C 291/00    (2006.01)
C07C 229/00    (2006.01)
C07C 247/00    (2006.01)

(52) U.S. Cl. ............... 562/567; 562/561; 562/433; 552/10

(58) Field of Classification Search ........ 562/512, 562/553, 561, 564, 567
See application file for complete search history.

(56) References Cited

U.S. PATENT DOCUMENTS 5,380,935 A * 1/1995 Takeya et al. ............ 562/567
5,907,058 A   5/1999 Moens
5,945,564 A * 8/1999 Takayanagi .............. 562/567

FOREIGN PATENT DOCUMENTS

EP    0845457 A1    6/1998

OTHER PUBLICATIONS

Ha et al., Synthetic Communications 24(18) 2557-2562 (1994).*
Ha et al., "Selective Bromination of Ketones. A Convenient Synthesis of 5-Aminolevulinic Acid," Synthetic Communications, 24(18):2557-62 (1994).

* cited by examiner

Primary Examiner—Karl Puttlitz
(74) Attorney, Agent, or Firm—Kriegsman & Kriegsman

(57) ABSTRACT

The present invention relates to 5-azido levulinic acid, a process for its preparation, its use. Using 5-azido levulinic acid as starting material for the synthesis of 5-amino levulinic acid hydrochloride it is possible to obtain the latter in good yield an in pharmaceutical acceptable quality. 5-Azido levuliniv acid is synthesized in that methyl 5-bromo levulinate and/or methyl 5-chloro levulinate is converted with aqueous hydrochloric acid and as a result of an incomplete bromine/chlorine exchange at the C-5-postion a mixture of 5-chloro levulinic acid and 5-bromo levulinic acid is obtained, and the obtained 5-chloro levulinic acid, a mixture of 5-chloro levulinic acid and 5-bromo levulinic acid and the pure 5-bromo levulinic acid is transferred into 5-azido levulinic acid by conversion with a nucleophilic azide.

7 Claims, No Drawings

5-AZIDO-LAEVULINIC ACID, METHOD FOR THE PRODUCTION THEREOF AND ITS USE

The present invention relates to 5-azido levulinic acid, a process for its preparation, its use for the preparation of 5-amino levulinic hydrochloride, and its use as explosive.

The importance of 5-amino levulinic acid hydrochloride as starting material for the synthesis of various compounds as well as its manifold employment, especially in the field of medicine, will be explained below.

5-Amino levulinic acid, storable as its halogen acid addition salt, in particular 5-amino levulinic acid hydrochloride, is a bioorganic compound, which appears as preliminary stage on the tetrapyrrole biosynthetic pathway of porphobilinogene, chlorophylle, haemine, vitamine $B_{12}$, and cytochrome (K. D. Gibson et al., Biochem. J. 1955, 61, 618; S. I. Beale, Plant Physiol. 1971, 48, 316; C. A. Rebeiz, Plant Physiol. 1970, 46, 543; A. I. Scott, Angew. Chem. 1993, 105, 1281-1302; Angew. Chem. Int. Ed. Engl. 1993, 32, 1223).

As known, these compound or its alkyl esters will be used as starting compound in the synthesis of a multitude of compounds.

5-Amino levulinic acid hydrochloride is used as substrate for the assay of 5-amino levulinic acid dehydratase (D. Shemin et al., Methods Enzymol. 1970, 17(A), 205; D. L. Coleman, ibid. 211; A. M. del C. Beatle et al., ibid., 216; P. Bodlaender et al., Anal. Biochem. 1974, 58, 500; D. Gurne, D. Shemin, Methods Enzymol. 1976, 44, 844), in acriculture as selective herbicide (5-amino levulinic acid hydrochloride: C. A. Rebeiz et al., Enzyme Microb. Technol. 1984, 6, 390; Chem. & Eng. News 1984, 62, 8; S. O. Duke, C. A. Rebeiz, Porphyric Pesticides: Chemistry, Toxikology, and Pharmaceutical Applications. ACS Symposium Series 559 1994; alkyl esters of 5-amino levulinic acid hydrochloride: H. Takeya, Jpn. Kokai Tokkyo Koho JP 0409360, 1992; Chem. Abstract. 1992, 116, 19755), as insecticide (C. A. Rebeiz et al., Pestic. Biochem. Physiol. 1988, 30, 11; A. I. Scott, Angew. Chem. 1993, 105, 1281-1302; Angew. Chem. Int. Ed. Engl. 1993, 32, 1223; S. O. Duke, C. A. Rebeiz, Porphyric Pesticides: Chemistry, Toxikology, and Pharmaceutical Applications. ACS Symposium Series 559 1994), and in various fields of medicine.

In the field of medicine, in particular the field of oncology, 5-amino levulinic acid hydrochloride is used for the treatment of actinic ceratosis with the help of photodynamic therapy (PDT) (Drugs Fut. 2000, 25(1), 74-76 and cited literature therein).

But also in photodynamic diagnostics (PDD), this includes some applications of the PDT, i.e. the fluorescence detection of some kinds of cancer like lung cancer, bladder cancer, and prostate cancer (WO 93/20810, WO 96/39188, WO 98/09155; A. G. Hofstetter, Springer Verlag, Berlin, Heidelberg, New York, London, Paris, Tokio, Hong Kong, Barcelona, Budapest, 1995.), as well as in marking brain tumors (W. Stummer et al., Neurosurgery 1998, 42(3), 518-526.) someone fall back on 5-amino levulinic acid hydrochloride.

A novel application concerns the photosensitation of arteries in combination with the baloon anglioplastics, which shall make an operative post treatment with hardening of the arteries unnecessary (New Scientist 1999, 162, Nr. 2185).

Recently, there was reported about the application of 5-amino levulinic acid hydrochloride as hair restorer (Shiseido Co., Ltd.; Cosmo Sogo Kenkyusho K. K., Jpn. Kokai Tokkyo Koho JP 11116, 446 [99116, 446], 1999; Chem. Abstract. 1999, 130, 356898z).

The big interest in 5-amino levulinic acid hydrochloride is also reflected by the great number of synthetic pathways described in the literature.

The discussion of the various processes must follow in view of the transferness to the technical production scale, so that this compound, which is useful in so many fields, can be prepared on a large scale, cost-effective and without pollution of the environment.

Some exemplary production processes of 5-amino levulinic acid hydrochloride, starting from different substance classes are discussed in the following.

U.S. Pat. No. 5,380,935 discloses a process, in which furfuryl amine, the amino function of which was protected, is oxidised by oxygen on the photochemical pathway in the precense of a sensetizer. Catalytic reduction of the intermediate and subsequent acid catalysed deprotection of the resulting product yielded 5-amino levulinic acid hydrochloride.

Some other processes make use of furane derivatives as starting material for the synthesis of 5-amino levulinic acid hydrochloride, also (EP-A 0607952; U.S. Pat. No. 5,284,973; U.S. Pat. No. 5,344,974; L. Cottier, G. Descotes, L. Eymard, K. Rapp, Synthesis 1995, 303-306; K. Suzuki et al., Nippon Kagaku Kaishi 1999, 3, 199-202).

All these processes have a great deal in common: The amino function has to be protected first, and in the last step of the synthetic sequence the protecting group has to be removed again. Partly, for the user and the environment, harmful solvents and chemicals are used, which have to be disposed cost-intensive after the reaction.

The use of expensive photosensetizers like fullerene (C60) or rose bengal is to be said against a technical application of these processes, too.

Alternatively, some succinyl derivatives—by introduction of an carbon-nitrogen moiety—are used for the synthesis of 5-amino levulinic acid hydrochloride.

In U.S. Pat. No. 3,846,490, e.g. mono methyl succinate mono chloride was reacted together with hippuric acid in γ-picoline as solvent. The obtained oxazolidine derivative is hydrolised with formation of 5-amino levulinic acid hydrochloride. Further processes, which start from succinic acid, are described by A. Pfaltz, Tetrahedron Lett. 1984, 25, 2977-2980 and A. Nudelman, A. Nudelman, Synthesis 1999, 5, 568-570.

Unfortunately, the single workup steps of these reaction sequences are expensive and result in side products, which have to be seperated. For the preparation of 5-amino levulinic acid hydrochloride according to the processes described here, toxic chemicals (i.e. zinc, copper cyanide) and solvents (i.e. γ-picoline) are used. The toxic side products, built up in parts of the synthesis, have to be disposed.

As well, pyridine derivatives are used as starting material for the synthesis of 5-amino levulinic acid hydrochloride. Starting from 2,5-dihydroxy pyridine, C. Herdeis et al. (Arch. Pharm. 1984, 317, 304-306) obtained a product by oxidation. Subsequent catalytic hydrogenation yielded 2,5-piperidone, which was converted into 5-amino levulinic acid hydrochloride by acidic hydrolysis. H. Takeya, K. Suzuki, K. Sasaki, Nippon Kagaku Kaishi 1999, 355-358 use 1,5-dihydroxy 2-pyridone as starting material for the preparation of 5-amino levulinic acid hydrochloride.

Concerning these reaction pathways, both oxidation and reduction steps are included. The poor yields reached in both processes be in an inconvenient proportion to the expense of the processes. Besides, the provision of large amounts of the needed pyridine derivatives turn into difficult.

The processes for the production of 5-amino levulinic acid hydrochloride, listed in the following, are starting with cheap and in large quantities available levulinic acid (production on a ton-scale: J. J. Bozell, L. Moens, D. C. Elliott, Y. Wang, G. G. Neuenschwander, S. W. Fitzpatrick, R. J. Bilski, J. L. Jarnefeld, Res. Cons. Recyc. 2000, 28, 227-239).

In U.S. Pat. No. 5,987,058, methyl 5-bromo levulinate, which is available by bromination of levulinic acid, is transferred to methyl 5-N,N-diformylamino levulinate. Subsequent acid catalysed hydrolysis yields 5-amino levulinic acid hydrochloride.

Alternative processes, starting with methyl 5-bromo levulinate have been described. In these processes the bromine at C-5 is exchanged by a nucleophilic nitrogen (potassium phthalimide: E. Benedikt, H.-P. Kost, Z. Naturforsch. 1986, 41b, 1593-1594; conversion with sodium azide: H.-J. Ha, S.-K. Lee, Y.-J. Ha, J. W. Park, Synth. Comm. 1994, 24(18), 2557-2562). In case of the substitution by an azide, the methyl 5-azido levulinate is obtained as an heavy oil.

In view of the further conversion to 5-amino levulinic acid hydrochloride by catalytic hydrogenation and simultaneous ester hydrolysis, it has to be guaranteed, that the azido ester is supplied in pure form.

Distillation of the azido ester without any decomposition is not possible and other purification steps, i.e. chromatographic processes, are very expensive, and therefore not recommendable for the technical scale.

Further disadvantage of the last described synthetic pathways lie on the difficult handling of methyl 5-bromo levulinate.

This compound is a liquid with strong lachrymatory properties. The compound is a strong skin irritant and further, in the presence of traces of acid, it has a tendency to the acid catalysed isomerisation into the compounds methyl 3-bromo-, methyl 3,5-dibromo- and methyl 5-bromo levulinate. This circumstance complicates the storage of the compound.

The substitution of bromine in methyl 5-bromo levulinate by an alkali metal imide or alkali azide yields sodium bromide as side product, which moderate to good solubility in organic solvents, especially lower alkanols, is well-known.

The production of sodium bromide free 5-amino levulinic acid hydrochloride therefore require partially expensive purification steps.

In particular in view of the use of 5-amino levulinic acid hydrochloride for medical purposes it must be secured, that the drug is very pure and free as less as possible from impurities deriving from inorganic salts.

A reaction pathway has to be chosen, which yields a pure product by a simple transformation starting with a pure starting material. Side reactions, whereby side products could be formed, and which have to be separated from the major product, should not occur.

In comparison to processes, that don't start with levulinic acid, the functionalisation with bromine at the C-5-position of levulinic acid offers the advantage, that 5-amino levulinic acid hydrochloride is available without any problems only in two steps starting with pure methyl 5-bromo levulinate. If pure reagents are used, no organic side products arise, which affect the further reaction pathway and have to be separated expensive.

As side products, only potassium bromide and in case of the hydrolysis of methyl 5-phthalimido levulinate and methyl 5-N,N-Diformyl levulinate, phthalic acid and formic acid, respectively, and methanol are build up, the disposition of which is unproblematic.

A reaction pathway, starting with pure levulinic acid derivatives like 5-bromo levulinic acid and particulary 5-chloro levulinic acid, transformation of these carboxylic acids in the next step by substitution of the halogen atom with an inorganic azide into 5-azido levulinic acid, and at least reduction of the azido functionality in 5-azido levulinic acid to the amino funtionality, is unknown so far.

The carboxylic acids 5-bromo- and 5-chloro levulinic acid are only difficult available on the classic pathway by means of bromination or chlorination of levulinic acid because of the lack of regioselectivity of the halogenation reaction. The desired levulinic acid derivatives are available in only poor yields.

But both compounds have the advantageous properties, that they are crystalline, non-lachrymatory and storable.

The transformation of 5-chloro levulinic acid with potassium azide is especially advantegous, because potassium chloride is the only harmless side product formed.

It is therefore an object of the present invention to provide a compound and a process for the preparation of this compound, while the employment of this compound for the preparation of 5-amino levulinic acid hydrochloride overcomes the disadvantages mentioned above.

This object is achieved by the provision of 5-azido levulinic acid.

5-Azido levulinic acid is a so far unknown compound and a new starting compound for the preparation of 5-amino levulinic acid hydrochloride.

Further object of the present invention is the use of 5-azido levulinic acid as starting compound for the cost-effective and high-yield preparation of 5-amino levulinic acid hydrochloride of pharmaceutical purity on a technical scale.

The provision of 5-azido levulinic acid allows the creation of an improved production process of 5-amino levulinic acid hydrochloride. The process makes the cost-effective and hield-yield production of 5-amino levulinic acid hydrochloride of pharmaceutical purity possible.

According to the invention this object is achieved by a process, which makes the preparation of 5-amino levulinic acid hydrochloride in pharmaceutical purity and in a four-step-process with an overall yield of 31-35% possible.

According to the inventive process, cost-effective starting compounds are used, and products, which have to be disposed are only hydrobromic acid, methanol and potassium chloride.

Surprisingly, a simple way for the preparation of 5-chloro levulinic acid from methyl 5-bromo levulinate was found.

Methyl 5-bromo levulinate, which is obtained by bromination of levulinic acid in methanol in a known manner, reacts quantitatively with aqueous hydrochloric acid under ester hydrolysis and simultaneous bromine/chorine-exchange at position C-5 to give 5-chloro levulinic acid. This transformation is unknown so far.

This compound represents an unlimited storable and excellently cristallising solid (m.p. 75° C.), which posesses no lachrymatory properties.

This compound is better suitable for the transformation with a nucleophilic nitrogen like sodium azide, because of the only side product formed is sodium chloride.

Sodium chloride itself is practically unsolulable in organic solvents and nontoxic.

In the following step, the so obtained 5-chloro levulinic acid will be dissolved in a suitable solvent and stirred with one equivalent of a suitable azide, in particular sodium azide.

In particular acetone, but if required also other organic solvents, such as dipolar aprotic solvents, substituted und unsubstituted amides, cylic and acyclic ethers and the like, may in principle be used as solvent for the reaction of the 5-chloro levulinic acid with a suitable azide.

However, the work with other solvents having a comparable dissolution behaviour, in particular solvents of high polarity, should not be ruled out.

As a new key compound, the so far unknown 5-azido levulinic acid arises in quantitative yield by means of nucleophilic substitution.

This new key compound represents a colorless, crystalline (m.p. 70-71° C.) and an unlimited and without any decomposition storable compound, if prepared according to the following process. The substance contains no inorganic material, it is not sensitive to impact, and it can be safely handled at room temperature.

Because of an uncomplete bromine/chlorine-exchange, 5-chloro levulinic acid may obtain as many as 8% of 5-bromo levulinic acid. But, the presence of small amounts of 5-bromo levulinic acid does not disturb the further reaction pathway, because this compound also reacts with a suitable inorganic azide, in particular sodium azide, in acetone as solvent with clean formation of 5-azido levulinic acid.

The conversion of 5-bromo levulinic acid, which was prepared on a different pathway, with sodium azide in acetone, after crystallisation from an organic solvent resulted in the formation of 5-azido levulinic acid in nearly quantitative yield. The compound was free of inorganic salts.

In the following step, the key compound 5-azido levulinic acid will be reduced to 5-amino levulinic acid hydrochloride without any difficulties. The reduction is preferably carried out as a catalytic hydrogenation in the presence of a metal catalyst (preferably palladium or platinum on a suitable carrier, such as active carbon) in aqueous hydrochloric acid without any arise of undesireable organic by-products. The catalyst can be regenarated. 5-Amino levulinic acid hydrochloride is obtained absolutly pure with an overall yield of 31-35% (starting from levulinic acid).

According to the present invention, the problem is solved by making 5-azido levulinic acid available, and providing a process for its preparation. The preparation process of 5-azido levulinic acid implies the conversion of methyl 5-bromo levulinate and/or methyl 5-chlor levulinate with aqueous hydrochloric acid. As a result of an incomplete bromine/chlorine-exchange at the C-5 postion, a mixture of 5-chloro- and 5-bromo levulinic acid is obtained. The obtained mixture of 5-chloro- and 5-bromo levulinic acid, 5-chloro levulinic acid, and pure 5-bromo levulinic acid will be transferred into 5-azido levulinic acid by conversion of the compounds with an nucleophilic azide.

It is preferred, according to the present invention, to carry out the conversion with an azide in a polar solvent, especially acetone, an $C_1$-$C_4$-alkanol or water as the reaction medium.

Furthermore, according to the present invention, the problem is solved by using 5-azido levulinic acid for the preparation of 5-amino levulinic acid hydrochloride, where 5-azido levulinic acid is transferred to 5-amino levulinic acid hydrochloride by catalytic hydrogenation.

In particular it is preferred to carry out the catalytic hydrogenation in aqueous hydrochloric acid, to remove the hydrogenation catalyst, to remove the solvent and excess hydrochloric acid by distillation, and to obtain 5-amino levulinic acid hydrochloride by crystallisation from 2-propanol or tert-butyl methylether/methanol.

Surprisingly it was found also, that 5-azido levulinic acid posseses explosive properties. Because of its chemical constitution, only nontoxic gases, namely nitrogen and carbon oxide, will be released as reaction substances. The released amount of gas is very large and will be increased by the exothermic reaction during explosion. 5-azido levulinic acid is sensitive to impact and detonates already at an impact energy of 40 J.

For this reason, 5-azido levulinic acid is especially suitable as priming fuse and as explosive for the operation of airbags in the motor vehicle industry.

The following examples explain the invention.

EXAMPLE 1

Preparation of 5-Chloro levulinic acid: A solution of 1 g (4.78 mmole) of methyl 5-bromo levulinate in 20 ml of 3 M hydrochloric acid was stirred at 70° C. until the reaction was finished (24 h, $^1$H-NMR control spectra showed only product signals). The solvent, excess hydrochloric acid, hydrobromic acid, and methyl alcohol were removed by distillation in in vacuo. To the residue 20 ml of methylene chloride was added and the resulting solution was dried over sodium sulfate. Evaporation of the solvent yielded 702 mg of a pale yellow solid. The solid was dissolved in 2 ml of tert-butyl methylether. Petroleum ether (40-60° C.) was added dropwise until crystallisation occured. The mixture was stirred for 0.5 h at ambient temperature and the crystals were filtered off.

Yield: 684 mg, 95% Melting point: 75° C.; an x-ray analysis study of the crystals confirms the structure of the compound. Elemental analysis: Calcd. C, 39.89, H, 4.69; Found C, 39.35, H, 4.67. IR (KBr): ν (cm$^{-1}$)=3500-2100, 1700 (C=O), 1440, 1410, 1370, 1330, 1290, 1210, 1140, 1090, 1030, 950, 865, 765, 730, 610. $^1$H-NMR (CDCl$_3$, 200 MHz): δ (ppm)=2.70 (t, $^3$J=6.7 Hz, 2H), 2.96 (t, $^3$J=6.7 Hz, 2H), 4.14 (s, 2H), 8.8 (br. s, 1H). $^{13}$C-NMR (CDCl$_3$, 50.3 MHz): δ (ppm)=27.7 (HOOC—CH$_2$), 34.0 (CH$_2$—CH$_2$—C=O), 48.0 (CH$_2$—Cl), 178.4 (COOH), 201.2 (C=O).

EXAMPLE 2

Preparation of a mixture of 5-chloro levulinic acid and 5-bromo levulinic acid: A mixture of 1 g (4.78 mmole) of methyl 5-bromo levulinate in 20 ml of 3 M hydrochloric acid was stirred for 12 h at 70° C. The solvent, excess hydrochloric acid, hydrobromic acid, and methyl alcohol was removed by distillation in vacuo. To the residue 20 ml of methylene chloride was added and the resulting solution was dried over sodium sulfate. Evaporation of the solvent yielded 740 mg of a pale yellow solid. The solid was dissolved in 2 ml of tert-butyl methylether. Petroleum ether (40-60° C.) was added dropwise until crystallisation occured. The mixture was stirred for 0.5 h at ambient temperature and the crystals filtered off.

Yield: 700 mg, 95% $^1$H-NMR: After integration of the 5-CH$_2$-proton signals of the mixture of 5-chloro levulinic acid and 5-bromo levulinic acid a ratio of 92:8 was found.

EXAMPLE 3

Preparation of 5-azido levulinic acid from 5-chloro levulinic acid: 5-Chloro levulinic acid (prepared as described in Example 1) and sodium azide were reacted with one another in a molar ratio of 1:1 in acetone. The reaction mixture was stirred at 50° C. until the end of the reaction ($^1$H-NMR control spectra showed only product signals). To the reaction mixture 20 ml of methylene chloride was added, the solid was filtered off, the filtrate was washed with 3 M aqueous sodium chloride and dried over sodium sulfate. Evaporation of the solvent yielded a pale yellow oil in quantitative yield. Crystalisation of the residue from methylene chloride/petroleum ether (40-60° C.) yielded pale yellow needles consisting of 5-azido levulinic acid.

Yield: 700 mg, 95% Melting point: 70-71° C. Elemental analysis: Calcd. C, 38.22; H, 4.49; N, 26.74; Found C, 38.39; H, 4.59; N, 26.07. IR (KBr): ν (cm$^{-1}$)=3350-2350, 2090 ($N_3$), 1725 (C=O), 1415, 1400, 1370, 1340, 1285, 1260, 1230, 1170, 1080, 1040, 1000, 930, 885, 830, 800, 685, 630. $^1$H-NMR (CDCl$_3$, 200 MHz): δ (ppm)=2.70 (s, 4H), 4.02 (s, 2H), 8.3 (br. s, 1H). $^{13}$C-NMR (CDCl$_3$, 50.3 MHz): δ (ppm)=27.4 (HOOC—CH$_2$), 34.1 (CH$_2$—CH$_2$—C=O), 57.5 (CH$_2$—N$_3$), 177.3 (COOH), 202.7 (C=O).

EXAMPLE 4

Preparation of 5-azido levulinic acid from a mixture of 5-chloro levulinic acid and 5-bromo levulinic acid: A mixture of 5-chloro and 5-bromo levulinic acid (0.5 g, prepared as described in Example 2) and sodium azide were reacted with one another in a molar ration of 1:1 in acetone. The reaction mixture was stirred at 50° C. until the end of the reaction ($^1$H-NMR control spectra showed only product signals). An amount of 20 ml of methylene chloride was added, the solid was filtered off, the filtrate was washed with 3 M aqueous sodium chloride and dried over sodium sulfate. Evaporation of the solvent yielded a yellow oil in quantitative yield. Crystalisation of the residue from methylene chloride/petroleum ether (40-60° C.) yielded pale yellow needles consisting of 5-azido levulinic acid.

Yield: 510 mg, 95%; the physical and spectroscopic data are in agreement with those obtained from the material prepared according to Example 3.

EXAMPLE 5

Preparation of 5-azido levulinic acid from 5-bromo levulinic acid: 5-bromo levulinic acid (prepared as described in Example 7) was dissolved in acetone. To the resulting solution was added sodium azide to a molar ratio of 1:1 (5-bromo levulinic acid:sodium azide) and the reaction mixture was stirred at 50° C. until the end of the reaction ($^1$H-NMR control). To the reaction mixture 20 ml of methylene chloride was added, the solid was filtered off, the filtrate was washed with 3 M aqueous sodium chloride and dried over sodium sulfate. Evaporation of the solvent yielded a pale yellow oil in quantitative yield. Crystalisation of the residue from methylene chloride/petroleum ether (40-60° C.) yielded pale yellow needles consisting of 5-azido levulinic acid.

Yield: 390 mg, 97% Melting point: 70-71° C.; the physical and spectroscopic data are in agreement with those obtained from the prepared according to Example 3.

EXAMPLE 6

Preparation of 5-amino levulinic acid hydrochloride by hydrogenation of 5-azido levulinic acid: 5-azido levulinic acid otained according to Example 3 was dissolved in 3 M hydrochloric acid, a hydrogenation catalyst (palladium on carbon) was added and the reaction mixture was hydrogenated for 5 h while passing in hydrogen at a pressure of 6 bar. By monitoring the hydrogenation it was found that the hydrogenation was completed quantitatively after 5 h ($^1$H-NMR control spectra showed only product signals). The catalyst was filtered off from the clear and colorless solution, and the reaction medium, hydrochloric acid, was removed by distillation in vacuo. To the resulting viscous, colorless residue 4 ml of 2-propanol was added while stirring. Alternatively, the residue was dissolved in 5 ml of methanol and an amount of 5 ml of tert-butyl methylether was added while stirring. In both cases colorless crystals were formed after a short time, which were filtered off. The obtained crystals were washed with acetone and dried in vacuo.

Yield: 709 mg, 95% Melting point: 150-151° C.; melting point data of various producers: 144-151° C.; Merck: 150-156° C.; Fluka: ~150° C. (decomposition); Aldrich: 156° C. (decomposition); Acros Organics 156-158° C. (decomposition).

The NMR data (A. Nudelman and A. Nudelman, *Synthesis* 1999, 4, 568-570) and chromatographic data (C. Herdeis, A. Dimmerling, *Arch. Pharm.* 1984, 317, 304-306) are in agreement with those given in the literature.

EXAMPLE 7

Preparation of 5-bromo levulinic acid: Levulinic acid (5.0 g, 43.1 mmole) was dissolved in 50 ml of carbon tertrachloride in a three-necked flask with a mechanical stirrer, a dropping funnel, a reflux condenser, and an internal thermometer. To the reaction mixture bromine (6.88 g, 43.1 mmole) was added dropwise during 0.5 h at ambient temperature. After decoloration of the orange reaction mixture 50 ml of water were added. The organic layer was separated, washed with brine, and dried over magnesium sulfate. Evaporation of the solvent yielded a yellow oil. From 50 ml of ether/petroleum ether (40-60° C.) colorless crystals are formed consisting of pure 5-bromo levulinic acid.

Yield: 900 mg, 9.5% Melting point: 79-80° C. IR (KBr): ν (cm$^{-1}$)=3500-2100, 1700 (C=O), 1430, 1400, 1350, 1300, 1280, 1240, 1100, 1050, 970, 920, 860, 760, 720, 610. $^1$H-NMR (CDCl$_3$, 200 MHz): δ (ppm)=2.70 (t, $^3$J=6.7 Hz, 2H), 2.96 (t, $^3$J=6.7 Hz, 2H), 3.95 (s, 2H), 8.5 (br. s, 1H). $^{13}$C-NMR (CDCl$_3$, 50.3 MHz): δ (ppm)=28.0 (HOOC—CH$_2$), 34.1 (CH$_2$—CH$_2$—C=O), 33.9 (CH$_2$—Cl), 178.0 (COOH), 200.4 (C=O).

The invention claimed is:
1. 5-azido levulinic acid.
2. Process for the preparation of 5-azidolevulinic acid, wherein
   (a) methyl 5-bromo levulmate and/or methyl 5-chloro levulinate is reacted with aqueous hydrochloric acid and as a result of an incomplete bromine/chlorine exchange at the C-5-postion a mixture of 5-chloro levulinic acid and 5-bromo levulinic acid is obtained, and
   (b) the obtained mixture of step (a) is converted to 5-azido levulinic acid by conversion with a nucleophilic azide.
3. Process according to claim 2, wherein in stage (b) the conversion with an azide is carried out in a reaction medium consisting of a polar solvent.

4. Process according to claim 2, wherein in stage (b) an alkali metal azide is used as nucleophilic azide.

5. A method of preparing 5-amino levulinic acid hydrochloride, wherein 5-azido levulinic acid is converted into 5-amino levulinic acid hydrochloride by catalytic hydrogenation.

6. The method according to claim 5, wherein (a) the catalytic hydrogenation ist carried out in aqueous hydrochloric acid, (b) the solvent and excess hydrochloric acid is seperated and (c) 5-amino levulinic acid hydrochloride is obtained by cristallisation from 2-propanol or t-butyl methyl ether/methanol.

7. Process according to claim 2, wherein in stage (b) a sodium azide is used as nucleophilic azide.

* * * * *